United States Patent [19]

Shida et al.

[11] Patent Number: 5,426,051

[45] Date of Patent: Jun. 20, 1995

[54] GENE FOR A-TYPE INCLUSION BODY OF POXVIRUS

[75] Inventors: Hisatoshi Shida; Shinichi Funahashi, both of Kyoto, Japan

[73] Assignee: Toa Nenryo Kogyo Kabushiki Kaisha, Tokyo, Japan

[21] Appl. No.: 587,546

[22] Filed: Sep. 24, 1990

Related U.S. Application Data

[63] Continuation of Ser. No. 99,765, Sep. 22, 1987, abandoned.

[30] Foreign Application Priority Data

Sep. 22, 1986 [JP] Japan ................... 61-222194
Sep. 9, 1987 [JP] Japan ................... 62-223972

[51] Int. Cl.$^6$ ............... C12N 15/86; C12N 15/39; C12N 7/01
[52] U.S. Cl. ............... 435/320.1; 536/23.72; 536/24.1; 536/24.2; 435/235.1
[58] Field of Search ............ 435/69.1, 69.3, 172.1, 435/172.3, 235.1, 320.1, 6, 7.1, 948; 935/6, 9, 11, 12, 32, 34, 57, 65, 70; 536/27, 23.72, 24.1, 24.2

[56] References Cited

U.S. PATENT DOCUMENTS

4,745,051  5/1988  Smith et al. ............... 435/69.51

FOREIGN PATENT DOCUMENTS

0083286  7/1983  European Pat. Off. .
0162782  11/1985  European Pat. Off. .

OTHER PUBLICATIONS

DeCarlos, A. et al. 1991. *Virology* vol. 185 pp. 768–778.

Cooper, J. A. et al. 1981. *J. Virology* vol. 37 pp. 284–294.
Patel, D. et al. 1986. Abstracts of papers presented at the 6th workshop on Poxvirus/Iridovirus. Cold Spring Harbor Laboratory, Cold Spring Harbor, N.Y., p. 25.
H. Amano et al., J. gen. Virol. 54, 203–207, 1981.
Patel et al (1986) Virology 149:174–189.
Robbins et al (1984) J Appl Mol Gen 2:485–496.
Boyle et al (1986) J Gen Virol 67:1591–1600.
Kitamoto et al (1986) Arch. Virol 89:15–28.
Wittek et al (1984) Nucleic Acids Res. 12:4835–4848.
Sugges et al (1981) PNAS 78:6613–6617.
Young, R. A. et al. 1983. *Proc. Nat. Acad. Sci. USA* vol. 80 pp. 1194–1198.
Chen, C. Y. et al. 1984. *Nucleic Acids Res* vol. 12 pp. 8951–8970.
Mellor, J. et al. 1985. *Gene* vol. 33 pp. 215–226.
J. Gen. Virol 67, (10) 2067–2082 (1986) M. Mackett et al. "Vaccinia Virus Expression Vectors".
Nucleic Acids Research, 12 (12), 4835–4848 (1984) R. Wittek et al. "Mapping of the Genes Coding for the Two Major Vaccinia Core Polypeptides".

*Primary Examiner*—Christine M. Nucker
*Assistant Examiner*—Mary E. Mosher
*Attorney, Agent, or Firm*—Michael N. Meller

[57] ABSTRACT

A gene fragment coding for a major protein of A-type inclusion body in poxvirus; a DNA fragment comprising an expression control region related to the gene; a plasmid comprising the gene and the expression control region for the gene; and a process for production of the above-mentioned gene or plasmid comprising the steps of a) preparing a poxvirus, b) preparing a viral DNA from the poxvirus, c) constructing a genomic DNA library from the viral DNA, and d) selecting a vector containing the gene coding for the major protein of A-type inclusion body from the genomic DNA library.

4 Claims, 15 Drawing Sheets

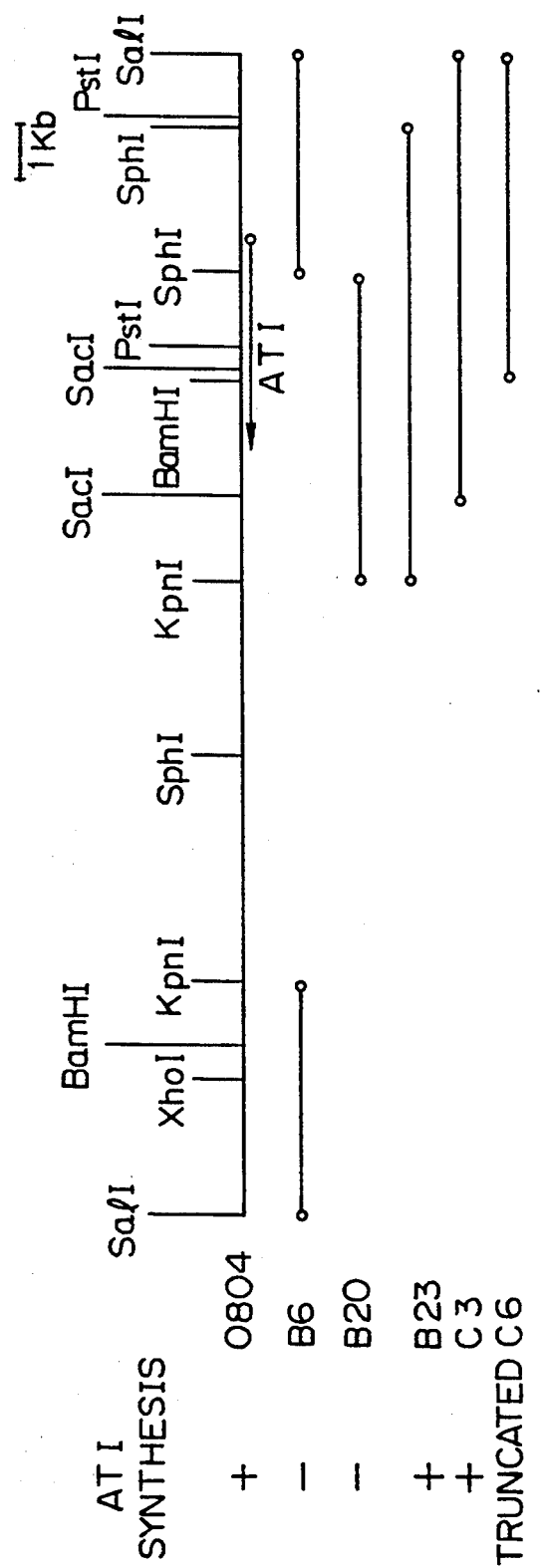

Fig. 3A

```
* -579
AAT.GCA.ACT.GAT.ACA.GGA.CAT.CAT.CAA.GAT.AGC.AAA.ATA.AAT.ATC.GAA.GTT.GAA.GAT.GAT   -520*
* -519                                                                              -460*
GAT.GAT.GAT.GAT.GAT.GAT.GAT.GAT.GAT.GAT.GTC.ATA.GAC.GAT.GAT.GAT.TAT.AAT.CCA.AAA.CCC.ACT.CCG   -400*
* -459                                                                              -340*
GAT.GAT.GAT.GAT.GAT.GAT.GAT.GTC.ATA.GAC.CCA.CCG.TTT.CCC.AGA.CAT.GAA.TAT.CAT.AAG.AGG.CCG.AAA
* -399                                                                              -280*
ATA.CCG.GAG.CCT.CAC.CCT.AGA.CCA.CCG.TTT.CCC.AGA.CAT.GAA.TAT.CAT.AAG.AGG.CCG.AAA
* -339                                                                              -220*
GTT.CTT.CCT.GTA.GAA.GAA.CCT.GAT.CCT.GTC.AAA.AAA.GAC.GCG.GAT.CGT.ATA.AGA.CTT.GAT
* -279                                                                              -160*
AAT.CAT.ATA.TTA.AAC.ACA.TTG.GAT.CAT.AAT.CTT.AAT.TCC.ATC.GGA.CAC.TAT.TGT.TGT.GAT
* -219                                                                              -100*
ACA.GCA.GCA.GTT.GAT.AGG.TTA.GAA.ATG.CAA.ACA.TTG.GGA.CAA.TAT.GCA.GTA.ATA
* -159                                                                              -40*
CTA.GCA.AGA.AAG.ATA.AAT.ATG.CAA.ACA.TTA.CTG.TTC.CCA.TTA.CCT.ACT.GTC.CAT
* -99                                                                               21*
CCA.CAT.GCG.ATA.GAT.GGT.AGT.ATT.CCG.CCA.CAT.GGG.AGA.TCT.ACG.ATC.TTA.TAA.TTA.CAC
* -39                        *1                                                      81*
GAT.TGT.AGT.TAA.GTT.TTG.AAT.AAA.ATT.TTT.TTA.TAA.TAA.ATG.GAG.GTC.ACG.AAC.CTT.ATT
                                                        Met-Glu-Val-Thr-Asn-Leu-Ile
                                                        ├──── Structural gene
* 22    Promotor region
GAA.AAA.TGT.ACC.AAG.CAC.TCC.AAA.GAT.TTC.GCC.ACT.GAG.GTA.AAA.CTA.TGG.AAC.GAT
Glu-Lys-Cys-Thr-Lys-His-Ser-Lys-Asp-Phe-Ala-Thr-Glu-Val-Lys-Leu-Trp-Asn-Asp
```

Fig. 3B

```
*  82                                                                                              141*
GAG.TTG.AGT.TCT.GAA.TCA.GGT.CTC.TCA.AGA.AAA.ACA.AGA.AAT.GTA.ATT.CGT.AAT.ATT.CTT
Glu-Leu-Ser-Ser-Glu-Ser-Gly-Leu-Ser-Arg-Lys-Thr-Arg-Asn-Val-Ile-Arg-Asn-Ile-Leu
* 142                                                                                              201*
CGT.GAT.ATC.ACT.AAG.TCA.CTA.ACT.ACA.GAT.AAG.AAA.TCA.AAG.TGT.TTC.CGT.ATA.CTA.GAA
Arg-Asp-Ile-Thr-Lys-Ser-Leu-Thr-Thr-Asp-Lys-Lys-Ser-Lys-Cys-Phe-Arg-Ile-Leu-Glu
* 202                                                                                              261*
CGT.TCG.ACG.ATT.AAC.GGA.GAG.CAG.ATT.AAA.GAT.GTA.TAT.AAA.ACT.ATT.TTT.AAT.AAT.GGT
Arg-Ser-Thr-Ile-Asn-Gly-Glu-Gln-Ile-Lys-Asp-Val-Tyr-Lys-Thr-Ile-Phe-Asn-Asn-Gly
* 262                                                                                              321*
GTT.GAT.GTG.GAG.TCT.AGA.ATC.AAC.ACT.ACA.GGA.AAG.TAT.GTT.CTA.TTT.ACA.GTT.ATG.ACT
Val-Asp-Val-Glu-Ser-Arg-Ile-Asn-Thr-Thr-Gly-Lys-Tyr-Val-Leu-Phe-Thr-Val-Met-Thr
* 322                                                                                              381*
TAT.GCT.GCT.GAA.CTA.CGA.CTC.ATT.AAG.TCA.GAC.GAG.ATA.TTC.GCT.CTT.CTA.TCA.AGA
Tyr-Ala-Ala-Glu-Leu-Arg-Leu-Ile-Lys-Ser-Asp-Glu-Ile-Phe-Ala-Leu-Leu-Ser-Arg
* 382                                                                                              441*
TTT.TTT.AAC.ATG.ATA.TGT.GAT.ATT.CAT.AGA.ATT.GGA.TGT.GGT.AAT.ATG.TTT.GTT.GGT
Phe-Phe-Asn-Met-Ile-Cys-Asp-Ile-His-Arg-Lys-Tyr-Gly-Cys-Gly-Asn-Met-Phe-Val-Gly
* 442                                                                                              501*
ATT.CCT.GCT.GCT.CTA.ATT.AAT.CTA.TTG.GAA.ATT.GAT.CAG.ATT.AAC.AAA.CTG.TTT.AGC.GTG
Ile-Pro-Ala-Ala-Leu-Ile-Asn-Leu-Leu-Glu-Ile-Asp-Gln-Ile-Asn-Lys-Leu-Phe-Ser-Val
* 502                                                                                              561*
TTT.AGT.ACA.AGA.TAT.GAC.GCC.AAG.ACA.TTC.ATA.TAC.ACT.GAA.TAT.TTT.CTT.TTC.CTT.AAC
Phe-Ser-Thr-Arg-Tyr-Asp-Ala-Lys-Thr-Phe-Ile-Tyr-Thr-Glu-Tyr-Phe-Leu-Phe-Leu-Asn
```

Fig. 3C

```
* 562                                                                                          621*
ATT.AAT.CAT.TAT.CTA.GTT.AGT.GGC.TCA.GAG.TTA.TTT.ATC.AAC.GTA.GCA.TAT.GGT.CCG
Ile-Asn-His-Tyr-Leu-Val-Ser-Gly-Ser-Glu-Leu-Phe-Ile-Asn-Val-Ala-Tyr-Gly-Pro
* 622                                                                                          681*
GCA.TCT.TTT.TCA.CCA.ATT.AGT.GTT.CCA.GAC.TAT.ATT.ATG.GAA.GCA.CTT.ACA.TTT.AAG
Ala-Ser-Phe-Ser-Ser-Pro-Ile-Ser-Val-Pro-Asp-Tyr-Ile-Met-Glu-Ala-Leu-Thr-Phe-Lys
* 682                                                                                          741*
GCA.TGC.GAC.CAT.ATT.ATG.AAA.TCT.GGA.GAT.CTA.AAA.TAT.ACA.TTT.ACT.AAA.AAG
Ala-Cys-Asp-His-Ile-Met-Lys-Ser-Gly-Asp-Leu-Lys-Tyr-Thr-Phe-Thr-Lys-Lys
* 742                                                                                          801*
GTT.AAG.GAT.CTG.TTT.AAT.ACT.AAA.TCT.GTT.TAT.CAA.TAC.GTT.AGA.CTT.CAT.GAA
Val-Lys-Asp-Leu-Phe-Asn-Thr-Lys-Ser-Val-Tyr-Gln-Tyr-Val-Arg-Leu-His-Glu
* 802                                                                                          861*
ATG.TCA.TAT.GAT.GGC.GTT.TCA.GAG.GAT.GAC.GAT.GAG.GTA.TTC.GCT.ATC.CTT
Met-Ser-Tyr-Asp-Gly-Val-Ser-Glu-Asp-Asp-Asp-Asp-Glu-Val-Phe-Ala-Ile-Leu
* 862                                                                                          921*
AAC.TTG.AGT.ATT.GAT.TCC.AGC.GTT.GAT.AGA.TAC.AGA.AAC.AGA.GTT.CTT.CTA.CTA.ACT.CCA
Asn-Leu-Ser-Ile-Asp-Ser-Ser-Val-Asp-Arg-Tyr-Arg-Asn-Arg-Val-Leu-Leu-Thr-Pro
* 922                                                                                          981*
GAA.GTT.GCG.TCT.CTT.AGA.AAA.GAA.TAT.TCA.GAC.GTA.GAA.CCC.GAT.TAT.AAA.TAC.TTG.ATG
Glu-Val-Ala-Ser-Leu-Arg-Lys-Glu-Tyr-Ser-Asp-Val-Glu-Pro-Asp-Tyr-Lys-Tyr-Leu-Met
* 982                                                                                          1041*
GAT.GAG.GAA.GTA.CCA.GCT.TAC.GAC.AAG.CAT.TTG.CCT.AAG.CCT.ATT.ACT.AAC.ACT.GGT.ATT
Asp-Glu-Glu-Val-Pro-Ala-Tyr-Asp-Lys-His-Leu-Pro-Lys-Pro-Ile-Thr-Asn-Thr-Gly-Ile
```

Fig. 3D

```
* 1042                                                                              1101*
GAA.GAA.CCG.CAC.GCT.ACT.GGA.GGA.GAT.AAG.GAA.GAA.CAA.GAA.CAA.CAA.CCA.GTT.AAG.GTT
Glu-Glu-Pro-His-Ala-Thr-Gly-Gly-Asp-Lys-Glu-Glu-Gln-Glu-Gln-Gln-Pro-Val-Lys-Val
* 1102                                                                              1161*
GTC.CAG.TCT.AAA.CCT.GAT.GAT.GGA.ATC.ACG.CCA.TAC.AAT.CCA.TTT.GAA.GAT.CCT.GAT.TAT
Val-Gln-Ser-Lys-Pro-Asp-Asp-Gly-Ile-Thr-Pro-Tyr-Asn-Pro-Phe-Glu-Asp-Pro-Asp-Tyr
* 1162                                                                              1221*
GTT.CCC.ACA.ATT.ACA.AAA.ACG.GTT.TTA.GGA.ATC.GCT.GAT.TAC.CAA.CTA.GTC.ATT.AAT.AAA
Val-Pro-Thr-Ile-Thr-Lys-Thr-Val-Leu-Gly-Ile-Ala-Asp-Tyr-Gln-Leu-Val-Ile-Asn-Lys
* 1222                                                                              1281*
CTA.ATT.GAA.TGG.TTA.GAT.AAA.TGC.GAG.GAA.AAT.GGT.GGA.GAG.TAT.AAG.ACA
Leu-Ile-Glu-Trp-Leu-Asp-Lys-Cys-Glu-Glu-Asn-Gly-Gly-Glu-Tyr-Lys-Thr
* 1282                                                                              1341*
GAG.TTG.GAA.GAA.GCC.AAG.AGA.AAA.CTC.ACC.GAA.TTG.AAT.CTA.GAA.CTT.AGT.GAT.AAA.CTC
Glu-Leu-Glu-Glu-Ala-Lys-Arg-Lys-Leu-Thr-Glu-Leu-Asn-Leu-Glu-Leu-Ser-Asp-Lys-Leu
* 1342                                                                              1401*
AGT.AAG.ATT.AGG.ACT.TTG.GAA.AGG.GAT.TCT.GTT.TAT.AAA.ACC.GAA.AGA.ATC.GAC.CGA.CTT
Ser-Lys-Ile-Arg-Thr-Leu-Glu-Arg-Asp-Ser-Val-Tyr-Lys-Thr-Glu-Arg-Ile-Asp-Arg-Leu
* 1402                                                                              1461*
ACA.AAA.GAG.ATC.AAA.GAA.CTC.AGG.GAT.ATT.CAA.AAT.GGG.ACA.GAT.GGT.TCA.GAT.TCA
Thr-Lys-Glu-Ile-Lys-Glu-Leu-Arg-Asp-Ile-Gln-Asn-Gly-Thr-Asp-Gly-Ser-Asp-Ser
* 1462                                                                              1521*
TCA.GAA.ATT.GAT.AAG.AAG.ACT.ATC.CGA.GAA.TTG.AGA.GAA.TCA.CTT.GAT.CGG.GAA.CGA.GAA
Ser-Glu-Ile-Asp-Lys-Lys-Thr-Ile-Arg-Glu-Leu-Arg-Glu-Ser-Leu-Asp-Arg-Glu-Arg-Glu
```

Fig. 3E

```
* 1522                                                                              1581*
ATG.CGC.ACA.GAA.CTA.GAA.AGG.GAA.CTG.GAT.CTG.ACT.ATT.AGG.GAT.GGA.AAG.GTA.GAA.GGA.TCT
Met-Arg-Thr-Glu-Leu-Glu-Arg-Glu-Leu-Asp-Leu-Thr-Ile-Arg-Asp-Gly-Lys-Val-Glu-Gly-Ser
* 1582                                                                              1641*
TGT.CAA.CGA.GAA.CTT.GAA.CTC.AGT.CGT.ATG.TGG.CTA.AAA.CAA.CGC.GAT.GAC.GAT.CTC.AGA
Cys-Gln-Arg-Glu-Leu-Glu-Leu-Ser-Arg-Met-Trp-Leu-Lys-Gln-Arg-Asp-Asp-Asp-Leu-Arg
* 1642                                                                              1701*
GCT.GAA.ATT.GAC.AAA.CGT.CGT.AAT.GTC.GAA.TGG.GAA.CTG.TCC.AGA.CTT.CGT.AGG.GAT.ATC
Ala-Glu-Ile-Asp-Lys-Arg-Arg-Asn-Val-Glu-Trp-Glu-Leu-Ser-Arg-Leu-Arg-Arg-Asp-Ile
* 1702                                                                              1761*
AAG.GAA.TGC.GAC.AAA.TAC.AAG.GAG.GAT.CTT.GAT.AAG.GCC.AAA.ACA.ACT.ATT.AGT.AAC.TAC
Lys-Glu-Cys-Asp-Lys-Tyr-Lys-Glu-Asp-Leu-Asp-Lys-Ala-Lys-Thr-Thr-Ile-Ser-Asn-Tyr
* 1762                                                                              1821*
GTG.AGC.AGA.ATC.AGT.ACT.CTA.GAA.TCA.GAA.ATT.GCT.AAA.TAT.CAA.CAA.GAT.AGG.GAC.ACG
Val-Ser-Arg-Ile-Ser-Thr-Leu-Glu-Ser-Glu-Ile-Ala-Lys-Tyr-Gln-Gln-Asp-Arg-Asp-Thr
* 1822                                                                              1881*
CTT.TCT.GTA.CGC.AGA.GAA.CTT.GAG.GAA.CGA.CGA.CGC.GTT.AGA.GAT.CTC.GAA.TCT
Leu-Ser-Val-Val-Arg-Arg-Glu-Leu-Glu-Glu-Arg-Arg-Val-Arg-Asp-Leu-Glu-Ser
* 1882                                                                              1941*
AGA.CTC.GAT.GAA.TGT.ACA.CGC.AAT.CAA.GAA.GAC.ACG.CAA.GAA.GTT.GAT.GCA.CTG.CGT.TCG
Arg-Leu-Asp-Glu-Cys-Thr-Arg-Asn-Gln-Glu-Asp-Thr-Gln-Glu-Val-Asp-Ala-Leu-Arg-Ser
* 1942                                                                              2001*
CGT.ATT.AGA.GAA.CTG.GAG.AAT.AAG.TTG.GCC.GAC.TGC.ATG.GAA.AGC.GGA.GGA.AAT.CTC
Arg-Ile-Arg-Glu-Leu-Glu-Asn-Lys-Leu-Ala-Asp-Cys-Met-Glu-Ser-Gly-Gly-Asn-Leu
```

Fig. 3F

```
* 2002                                                                                              2061*
ACA.GAG.ATT.AGC.AGA.CTC.CAA.TCT.AGA.ATC.TCA.GAT.CTT.GAA.AGA.CAA.CTG.CGT.GAA.TGC
Thr-Glu-Ile-Ser-Arg-Leu-Gln-Ser-Lys-Ile-Ser-Asp-Leu-Glu-Arg-Gln-Leu-Arg-Glu-Cys
* 2062                                                                                              2121*
CGT.GGA.AAT.GCT.ACA.GAG.ATT.AGC.AGA.CTC.CAA.TAT.AGA.ATC.ACA.GAT.CTT.GAA.AGA.CAA
Arg-Gly-Asn-Ala-Thr-Glu-Ile-Ser-Arg-Leu-Gln-Tyr-Arg-Ile-Thr-Asp-Leu-Glu-Arg-Gln
* 2122                                                                                              2181*
CTG.AAC.GAC.TGT.AGA.CGT.AAT.AAT.GAG.AAC.AAT.GCC.GAT.ACA.GAA.AGA.GAG.ATG.CAA.CGT
Leu-Asn-Asp-Cys-Arg-Arg-Asn-Asn-Glu-Asn-Asn-Ala-Asp-Thr-Glu-Arg-Glu-Met-Gln-Arg
* 2182                                                                                              2241*
CTT.AGA.GAT.AGA.ATC.ACG.GAT.CTT.GAA.AGG.CAG.TTG.AGT.GAC.TGC.AGA.CGT.AAT.AAT.GAA
Leu-Arg-Asp-Arg-Ile-Thr-Asp-Leu-Glu-Arg-Gln-Leu-Ser-Asp-Cys-Arg-Arg-Asn-Asn-Glu
* 2242                                                                                              2301*
AGC.AAT.GCT.GAT.ATG.GAA.AGA.GAG.ATG.CAA.CGT.CTT.AGA.GAT.AGA.ATC.ATG.GAT.CTT.GAT
Ser-Asn-Ala-Asp-Met-Glu-Arg-Glu-Met-Gln-Arg-Leu-Arg-Asp-Arg-Ile-Met-Asp-Leu-Asp
* 2302                                                                                              2361*
AGA.CAG.CTT.AAC.GAA.TGT.AAA.CGC.GAC.GGT.AAC.GGA.ACA.TCT.TCT.GAG.GAG.GTA.AAT.AGG
Arg-Gln-Leu-Asn-Glu-Cys-Lys-Arg-Asp-Gly-Asn-Gly-Thr-Ser-Ser-Glu-Glu-Val-Asn-Arg
* 2362                                                                                              2421*
CTA.AAG.ACT.AGA.ATC.AGG.GAT.CTT.GAA.CGA.TCT.CTA.GAG.ATC.TGC.TCA.AAG.GAT.GAA.TCA
Leu-Lys-Thr-Arg-Ile-Arg-Asp-Leu-Glu-Arg-Ser-Leu-Glu-Ile-Cys-Ser-Lys-Asp-Glu-Ser
* 2422                                                                                              2481*
GAA.CTC.TAT.TCA.GCA.TAT.AAG.AGT.GAA.CTC.GGA.CGT.GCA.AGG.GAA.CAA.ATT.AGT.AAC.CTG
Glu-Leu-Tyr-Ser-Ala-Tyr-Lys-Ser-Glu-Leu-Gly-Arg-Ala-Arg-Glu-Gln-Ile-Ser-Asn-Leu
```

Fig. 3G

```
* 2482                                                                                           2541*
CAA.GAA.AGT.CTA.CGT.AGA.GAG.CGT.GAA.TCT.GAC.AAA.ACC.GAT.AGT.TAC.AGG.AGG.AGG.GAA
Gln-Glu-Ser-Leu-Arg-Arg-Glu-Arg-Glu-Ser-Asp-Lys-Thr-Asp-Ser-Tyr-Arg-Arg-Arg-Glu
* 2542                                                                                           2601*
TTG.ACT.CGT.GAA.AGA.AAT.AAA.ATC.GTA.GAA.TTG.GAA.AAA.GAA.CTT.AAT.AAG.TGT.TTC.GAT
Leu-Thr-Arg-Glu-Arg-Asn-Lys-Ile-Val-Glu-Leu-Glu-Lys-Glu-Leu-Asn-Lys-Cys-Phe-Asp
* 2602                                                                                           2661*
ACC.AAT.CAT.GCC.AAG.TAC.ATC.GAC.GAA.ATC.AAT.TCC.AAG.AAA.ACC.CGT.ATT.TCT.GAT.CTC
Thr-Asn-His-Ala-Lys-Tyr-Ile-Asp-Glu-Ile-Asn-Ser-Lys-Lys-Thr-Arg-Ile-Ser-Asp-Leu
* 2662                                                                                           2721*
GAA.CGA.CAA.CTA.GCA.GCC.TGT.AAA.TCT.AAT.GGT.GGT.AGC.AAT.GGA.GAC.ATG.GAC.CAA.TAC
Glu-Arg-Gln-Leu-Ala-Ala-Cys-Lys-Ser-Asn-Gly-Gly-Ser-Asn-Gly-Asp-Met-Asp-Gln-Tyr
* 2722                                                                                           2781*
AAA.CGG.GAA.ATT.GAA.TCT.CTT.AAA.CGC.GAG.CTC.GCC.GAG.TGT.AGA.CGT.GGT.AAC.AAT.GGA
Lys-Arg-Glu-Ile-Glu-Ser-Leu-Lys-Arg-Glu-Leu-Ala-Glu-Cys-Arg-Arg-Gly-Asn-Asn-Gly
* 2782                                                                                           2841*
TCC.CAT.AGT.GAT.TGT.AAG.TAC.TAT.GAC.GAA.GAA.GCA.AGA.GAG.GAA.GTT.AAG.AGA.TTG.CGT
Ser-His-Ser-Asp-Cys-Lys-Tyr-Tyr-Asp-Glu-Glu-Ala-Arg-Glu-Glu-Val-Lys-Arg-Leu-Arg
* 2842                                                                                           2901*
CAA.GAG.CTG.ACT.CAA.TTG.CAT.GAA.GAG.CTT.AAA.CGT.GCC.AGG.GAA.TCA.GAT.AAA.AAT.GAT
Gln-Glu-Leu-Thr-Gln-Leu-His-Glu-Glu-Leu-Lys-Arg-Ala-Arg-Glu-Ser-Asp-Lys-Asn-Asp
* 2902                                                                                           2961*
AGT.TAC.TAC.AAG.AGA.CAA.AGA.CAA.CGC.GCT.AAA.GTT.ATT.GAG.GTC.GAA.AAG.GAG
Ser-Tyr-Tyr-Lys-Arg-Gln-Arg-Ala-Lys-Val-Ile-Glu-Val-Glu-Lys-Glu
```

Fig. 3H

```
* 2962                                                                                                    3021*
CTG.GAA.AGA.TAT.TTC.GAC.GAC.AGT.AGA.CTC.GCG.GAA.TGT.AAA.AGG.CAT.GGG.GAT.GAA.ATG
Leu-Arg-Tyr-Phe-Asp-Asp-Ser-Arg-Leu-Ala-Glu-Cys-Lys-Arg-His-Gly-Asp-Glu-Met
* 3022                                                                                                    3081*
TTG.AGA.AAG.ATT.GCC.GAT.CTA.GAA.AAG.AAA.CTT.AGA.GAT.GGT.GGT.AAT.GGA.AAC.GGA.GGA
Leu-Arg-Lys-Ile-Ala-Asp-Leu-Glu-Lys-Lys-Leu-Arg-Asp-Gly-Gly-Asn-Gly-Asn-Gly-Gly
* 3082                                                                                                    3141*
AAC.GGT.TGC.ACA.TCC.AGC.TGT.GAA.TTC.GAA.AGA.AAA.ATC.GCC.GTC.CTA.GAA.GTT.GAA
Asn-Gly-Cys-Thr-Ser-Ser-Cys-Glu-Phe-Glu-Arg-Lys-Ile-Ala-Val-Leu-Glu-Val-Glu
* 3142                                                                                                    3201*
GTT.CGG.AAA.TCT.ATG.GAA.ACA.ATC.AAA.TCT.TTG.GAG.AAG.TTT.ATG.GAG.TTC.GAT.CGT.CTT
Val-Arg-Lys-Ser-Met-Glu-Thr-Ile-Lys-Ser-Leu-Glu-Lys-Phe-Met-Glu-Phe-Asp-Arg-Leu
* 3202                                                                                                    3261*
CAG.AAA.GAC.TGC.GCT.GAT.AGA.CTC.GAT.AAA.CTC.CGT.AAA.GAG.AAG.CGC.ATG.AAG.GCT.GAA.CGT
Gln-Lys-Asp-Cys-Ala-Asp-Lys-Leu-Asp-Lys-Leu-Arg-Lys-Glu-Lys-Arg-Met-Lys-Ala-Glu-Arg
* 3262                                                                                                    3321*
GAT.CTG.GAA.CGT.AGT.GAA.CGT.GAA.ATC.GCT.CGT.AAA.AAC.TGC.GGA.GGT.AAC.CCA.TGC.GAA.CGT.GAA.TTG
Asp-Leu-Glu-Arg-Ser-Glu-Arg-Glu-Ile-Ala-Arg-Lys-Asn-Cys-Gly-Gly-Asn-Pro-Cys-Glu-Arg-Glu-Leu
* 3322                                                                                                    3381*
GAA.TCT.GAA.CGT.AGT.GAA.AGA.GAA.CTG.AAG.AGG.TTG.GAA.TAT.CAA.CTA.GAT.GCG.GAG.AAA.GAA.AAA
Glu-Ser-Glu-Arg-Ser-Glu-Arg-Glu-Leu-Lys-Arg-Leu-Glu-Tyr-Gln-Leu-Asp-Ala-Glu-Lys-Glu-Lys
* 3382                                                                                                    3441*
GTT.AAG.TTC.TAC.AAA.AGA.GAA.CTA.GAA.CGT.GAT.CGG.TAT.CTT.TCT.AGT.AGA.TAT.CTT.ACC
Val-Lys-Phe-Tyr-Lys-Arg-Glu-Leu-Glu-Arg-Asp-Arg-Tyr-Leu-Ser-Ser-Arg-Tyr-Leu-Thr
```

Fig. 3I

```
* 3442                                                                              3501*
TCT.TCT.TCA.GAT.CCA.GAC.GAG.AAA.CCA.TTA.CCA.AAT.TAT.ACA.TTT.CCT.CGC.ATT.GAA.GTA
Ser-Ser-Ser-Asp-Pro-Asp-Glu-Lys-Pro-Leu-Pro-Asn-Tyr-Thr-Phe-Pro-Arg-Ile-Glu-Val
* 3502                                                                              3561*
GAA.CCG.TTG.ACG.ACT.GAG.GAT.ACA.GAA.CCA.AAA.CCT.GTA.GAA.GTG.CCT.CCA.TCG.TCC
Glu-Pro-Leu-Thr-Thr-Glu-Asp-Thr-Glu-Pro-Lys-Pro-Val-Glu-Val-Val-Pro-Pro-Ser-Ser
* 3562                                                                              3621*
GAC.GTT.ACT.GAA.CCA.ATT.AGT.AGT.GGT.GTA.ACA.CCA.TCG.GTG.GAT.GCC.GAA.CCA.GAA.CAT
Asp-Val-Thr-Glu-Pro-Ile-Ser-Ser-Gly-Val-Thr-Pro-Ser-Val-Asp-Ala-Glu-Pro-Glu-His
* 3622                                                                              3681*
CCA.CAG.CTT.TCT.GAA.TAT.CAG.ATT.TCG.GTA.TCT.CAA.GTA.GCT.GTT.ACA.CCT.CCA.CCA.AAA
Pro-Gln-Leu-Ser-Glu-Tyr-Gln-Thr-Ser-Val-Ser-Gln-Val-Ala-Val-Thr-Pro-Pro-Pro-Lys
* 3682                                                                              3741*
CCT.GAA.ACT.CCA.CAG.ATT.TCC.GAA.TAT.CAG.GAT.TAT.AGC.GAA.CTC.TAT.TCT.GCG.AGT.AAC
Pro-Glu-Thr-Pro-Gln-Ile-Ser-Glu-Tyr-Gln-Asp-Tyr-Ser-Glu-Leu-Tyr-Ser-Ala-Ser-Asn
* 3742                                                                              3801*
AAT.ACC.GAA.TCC.AAA.AAT.GTG.TTT.AGT.GAA.TTA.GCT.TAT.CTT.GAT.GAT.CTT.GAT.AAA.CTT
Asn-Thr-Glu-Ser-Lys-Asn-Val-Phe-Ser-Glu-Leu-Ala-Tyr-Leu-Asp-Asp-Leu-Asp-Lys-Leu
* 3802                                                                              3861*
GAT.GAT.ATT.GAT.GAG.TAT.CTA.AAC.AAT.ATT.ATG.CCA.GAA.AAG.ACG.GTT.TGA.GAT.CAA
Asp-Asp-Ile-Asp-Glu-Tyr-Leu-Asn-Asn-Ile-Met-Pro-Glu-Lys-Thr-Val-***
* 3862                                   3921*
                                    ├──Structural Gene──┤
CTT.TAT.CTA.ATG.GTT.TAT.AAA.ACG.AAG.GAG.GTC.TTC.GTT.CGA.AAT.CTA.ATT.TGA.CTT.TTA
```

```
* 3922                                                                    3981*
CGC.CTC.TGG.CAT.TCA.TTT.GAG.TAA.GAA.ATA.CTT.TAG.ATA.CGT.GCG.TGG.TAT.CAA.TTT.TTG
* 3982                                                                    4041*
TTA.AGA.GAG.GAG.AGA.GAT.TAA.GTT.TTG.AAC.ATC.TAA.GAC.ATG.TAT.TAA.TAC.CTT.TGA.TTT
* 4042
CTG.CTA.TGT.CTC.CAC.AAT.TTT.
```

Fig. 3J

GENE FOR A-TYPE INCLUSION BODY OF POXVIRUS

This is a file wrapper continuation of U.S. Ser. No. 099,765, filed Sep. 22, 1987, now abandoned.

BACKGROUND OF THE INVENTION

1. Field of the Invention

The present invention relates to a gene for an A-type inclusion body (ATI) of poxvirus. More specifically, it relates to a structural gene coding for a major protein of A-type inclusion body and a promoter necessary for the expression of the structural gene.

2. Description of the Related Art

Vaccines currently used include attenuated vaccines using attenuated living viruses or bacteria and inactivated vaccines using inactivated viruses or bacteria.

The attenuated vaccines have advantages in that they induce not only a humoral immune response but also a cell-mediated immune response, which responses are relatively high and can be produced at a low cost. However, sometimes side effects although occur even though these vaccines are attenuated. Moreover, there are various pathogens which have not been attenuated, and therefore, the attenuated vaccines are not universal for all kinds of pathogens.

On the other hand, although inactivated vaccines are relatively safe, they are disadvantageous in that they have a lower effectiveness.

In contrast with these conventional vaccines, new types of vaccines involving gene recombination technology are now under development. According to one of these techniques, an antigen gene of a pathogen is introduced to a plasmid, which is then used to transform bacterium such as *Escherichia coli* or yeast. The resulting transformant is then cultured to produce a large amount of an antigen protein, which is then recovered and purified to produce a vaccine. In this technique, once a small amount of antigen gene is obtained, it becomes easy to produce a large amount of vaccine which is not pathogenic. However, some problems relating to purifying method of the antigen protein, the selecting of an adjuvant used for the antigen protein, and the like, are yet unsolved. In another technique involving gene recombination technology, an antigen gene derived from a pathogen is introduced to a nonessential region of a vaccinia virus gene to construct a recombinant vaccinia virus containing the exogeneous gene, and the recombinant virus is used as a live vaccine. These vaccines essentially fall under the category of conventional live vaccines, and therefore, possess the advantages of the conventional live vaccine. Moreover, according to this technique, the use of an attenuated vaccinia virus as a vector provides safe vaccines with a low toxicity. In addition, this technique is universal in that a vaccine against any kind of pathogen can be produced. This advantage is not found in conventional vaccines.

According to a typical procedure of this technique, a gene coding an antigen protein of interest (antigen gene) is separated from a pathogen in question, and the antigen gene is cloned in a conventional *E. coli* plasmid. On the other hand, a nonessential region of gene of vaccinia virus or related virus is separated, and the nonessential region is introduced to an appropriate plasmid such as *E. coli* plasmid. The above-mentioned antigen gene is then inserted into the nonessential region of the plasmid to construct a recombinant plasmid, and next, the nonessential gene region of the virus origin interrupted with the antigen gene is recombined with a corresponding region of a gene of the vaccinia virus as a vector, to construct a recombinant vaccinia virus having a gene containing the target antigen gene. If the recombinant virus injected to a host such as a human or other animal can express the exogeneous antigen gene in an amount sufficient to generate an immune response in the host, the recombinant virus can be used as an attenuated vaccine.

Note, since the attenuation of a virus and the generation of an immune response are mutually exclusive phenomena, serious efforts are being made to develop a strong virus promoter which can sufficiently express an exogeneous gene in an attenuated virus.

SUMMARY OF THE INVENTION

Accordingly, the present invention provides a gene which is nonessential for a proliferation of poxvirus and homologous with a corresponding gene of a vaccinia virus, and therefore, can be used for the construction of a recombinant vaccinia virus, and an expression control region for said gene.

More particularly, the present invention provides a gene fragment coding for a major protein of A-type inclusion body in poxvirus.

The present invention also provides a DNA fragment comprising an expression control region related to the above-mentioned gene.

The present invention further provides a plasmid comprising a region coding for a major protein of A-type inclusion body in poxvirus, and an expression control region for the coding region.

The present invention also provides a method for the production of the above-mentioned gene or plasmid, comprising the steps of:
a) preparing poxvirus;
b) preparing viral DNA from the poxvirus;
c) constructing a genomic DNA library from the viral DNA; and
d) selecting a vector containing the gene coding for a major protein of A-type inclusion body from the genomic DNA library.

BRIEF DESCRIPTION OF THE DRAWINGS

FIG. 2 represents restriction enzyme cleavage maps of a SalI 22 Kb fragment in a plasmid p0804, a B6 fragment in a plasmid pB6, a B20 fragment in a plasmid pB20, a B23 fragment in a plasmid pB23, a C3 fragment in a plasmid pC3, and a C6 fragment in a plasmid pC6, all selected or derived from a genomic DNA library of cowpox virus;

FIGS. 3A to 3J represent a nucleotide sequence of a gene region encompassing a structural gene for a major protein of A-type inclusion body and a promoter region;

DESCRIPTION OF THE PREFERRED EMBODIMENT

As described above, to construct recombinant vaccinia viruses for vaccines, it is necessary to obtain a nonessential region of a viral gene into which an exogeneous antigen gene can be inserted, and a strong viral promoter. The present inventors found that a gene region coding for a major protein of A-type inclusion body in poxvirus satisfies the requirement for the above-mentioned nonessential gene region, and a promoter for expression of the gene region coding for the protein of A-type inclusion body satisfies the requirement for the above-mentioned promoter.

Origin of gene

A gene region coding for the protein of A-type inclusion body and an expression control region for expression of said coding region can be obtained from a poxvirus gene. Within the present invention, poxvirus includes all individual viruses belonging to the family Poxvirus, and is preferably cowpox virus belonging to the genus Orthopoxvirus. The A-type inclusion body gene is expressed in cells infected by the virus after maturation of the virus, and the gene expression product forms large inclusion bodies in the cytoplasm of the infected cells, and mounts 4% of the total protein in the cell. This means that the promoter present upstream of this gene is very strong, and therefore, the promoter is adequate as a promoter of the present invention for expression of an exogeneous antigen gene.

On the other hand, among poxviruses, those which do not form A-type inclusion bodies are present. This means that the A-type inclusion body gene is not essential for a proliferation of the virus, and therefore, the A-type inclusion body gene is most promising as a region to which an exogeneous antigen gene can be inserted.

Cloning of gene

Next, a procedure for cloning the present gene is described in detail, taking cowpox virus as an example.

(1) Purification of cowpox virus $5\times10^8$ of Vero cells (cells derived from renal cells of African green monkey) were infected with cowpox virus CPRO6 at an m.o.i. of 0.2, and the virus was recovered two days after the infection when the cytotoxicity became remarkable. The virus was then purified by sucrose density-gradient centrifugation to obtain about 3 mg of the virus.

(2) Purification of cowpox virus DNA

Three mg of the purified virus was digested with 1 mg/ml of proteinase K at 37° C. overnight in the presence of 0.5% sodium dodecyl sulfate (SDS) and 1 mM of ethylenediaminetetraacetic acid sodium salt (EDTA). The digest was extracted three times with phenol/chloroform and three times with ethyl ether to eliminate proteins. To the extracted digest was added 1/10 volume of 3M sodium acetate and two volumes of isopropanol, and the mixture was stirred with a glass rod to recover flocculated DNA on the rod. The recovered DNA was dissolved in a TE buffer (10 mM Tris-HCl, pH 8.0, 1 mM EDTA) and 180 μg of DNA was obtained.

(3) Construction of genomic DNA library from cowpox virus

Ten μg of the cowpox virus DNA prepared as above was cleaved with a restriction endonuclease HindIII or SalI in a buffer containing 10 mM Tris-HCl (pH 7.5), 60 mM NaCl and 7 mM $MgCl_2$, or a buffer containing 10 mM Tris-HCl (pH 7.5), 150 mM NaCl, and 7 nM $MgCl_2$, respectively, at 37° C. for 120 minutes. The HindIII-cleaved DNA was mixed with a plasmid pUC18 which had been cleaved with HindIII; and the SalI-cleaved DNA was mixed with a plasmid pUC13 which had been cleaved with SalI, and each of the mixtures was subjected to ligation in a buffer containing 66 mM Tris-HCl (pH 7.5), 5 mM $MgCl_2$, 5 mM dithiothreitol and 1 mM ATP using a T4 DNA ligase at 16° C. for 16 hours. The ligation mixture was used to transform *E. coli* JM103 or *E. coli* JM109 to prepare genomic DNA libraries of the cowpox virus, Each recombinant plasmid contained a genomic DNA fragment of about 1 Kb to 25 Kb.

(4) Identification of DNA containing A-type inclusion body gene

The plasmids containing a cowpox virus DNA fragment were transfected to CV-1 cells which had been infected with vaccinia virus, and expression of the A-type inclusion body gene in the transfected cells was confirmed by Western blotting to identify DNA containing an A-type inclusion body gene.

Namely, $3\times10^5$ of CV-1 cells (cells from monkey kidney) were infected with a vaccinia virus WR strain at an m.o.i. of 50 and allowed to stand for one hour. A plasmid containing the cowpox virus DNA was extracted from 2 ml of *E. coli* culture by an alkaline extraction method, and 10 μg of the plasmid DNA was transfected to cells previously infected with the vaccinia virus. After standing for 30 minutes at room temperature, 3 ml of a medium containing 5% fetal calf serum was added to the culture, which was then incubated at 37° C. for 5 hours, and after an exchange of the medium incubated at 37° C. overnight. After sonication of the cell suspension, the sonicate was subjected to SDS-polyacrylamide gel electrophoresis, and the gel was subjected to Western blotting. That is, proteins on the gel were electrophoretically transferred to a nitrocellulose filter. The nitrocellulose filter was treated with a buffer containing 10 mM Tris-HCl (pH 7.5), 0.15M NaCl and 5% bovine serum albumin, and reacted with an anti-A-type inclusion body antibody in a buffer containing 10 mM Tris-HCl (pH 7.5) and 0.15M NaCl at 37° C. for one hour. Next, the filter was reacted with an anti-rabbit IgG antiserum conjugated with peroxidase at 37° C. in the same buffer as described above, and finally, treated with a 10 mM Tris-HCl (pH 7.5) buffer containing 0.01% hydrogen peroxide, 0.5 mg/ml 4- chloronaphthol and 0.15M NaCl to develop an A-type inclusion body gene expression product. As a result, a SalI fragment of 22 Kb was found to contain the A-type inclusion body gene. This fragment was designated as 0804, and the plasmid containing this fragment was designated as p0804.

The plasmid p0804 was digested with SalI, and the resulting SalI fragment was cleaved with a restriction endonuclease KpnI, SphI, PstI or SacI. Each fragment thus obtained was ligated with a plasmid pUC 18 or plasmid pUC 19, which had been cleaved with a corresponding restriction endonuclease to obtain recombinant plasmids pB6, pB20, pB23, pC3, pC6, etc.

These plasmids were then tested for the presence of an A-type inclusion body gene therein, and it was confirmed that a KpnI-SphI fragment of 9.1 Kb in the plasmid pB23, and a SacI-SalI fragment of 8.9 Kb in the plasmid pC3 included an entire gene for a major protein of A-type inclusion body; and a SacI-SalI fragment of 6.2 Kb in the plasmid pC6 included a part of a gene for a major protein of A-type inclusion body.

The above-mentioned result is summarized in FIG. 1. FIG. 1 shows the result of Western blotting of SDS-polyacrylamide gel electrophoresis of cell suspensions prepared by transfecting the plasmids p0804, pB6, pB20, pB23, pC3 or pC6 to cells previously infected with vaccinia virus. Lanes 5, 6, 7, 8, 9 and 10 represent results for the plasmids p0804, pB6, pB20, pB23, pC3, and pC6, respectively. Lanes 1, 2 and 3 represent results obtained according to the same procedure as described above except that cells infected with the vaccinia virus WR strain, cells coinfected with the vaccinia virus WR strain and cowpox virus CPRO6 strain, and cells infected with cowpox virus were used, respectively, in place of the recombinant plasmid-transfected cells. Lane 4 is a result obtained from cells transfected with a plasmid pUC13 not containing a gene fragment of the virus. Upper bands corresponding to 160,000 Daltons of lanes 2, 3, 5, 8 and 9 represent an A-type inclusion body protein of cowpox virus, and lane 10 shows a band corresponding to 110,000 Daltons of an A-type inclusion body protein. This means that the plasmid pC6 contains a part of an A-type inclusion body gene, and therefore, cannot produce a protein of 160,000 Daltons. The lower bands corresponding to 94,000 Daltons in lanes 1, 2, and 4 to 10 represent an A-type inclusion body related-gene product of a vaccinia virus detected by the anti-A-type inclusion body antibody.

FIG. 2 represents restriction enzyme cleavage maps of the SalI 22 Kb fragment (0804) in the plasmid p0804, an A-type inclusion body gene-containing fragment B23 in the plasmid pB23, an A-type inclusion body gene-containing fragment C3 in the plasmid pC3, and an A-type inclusion body gene-containing fragment C6 in the plasmid pC6. FIG. 2 also represents positions of gene fragments inserted in the plasmids pB6 and pB20, which could not express the A-type inclusion body.

*Escherichia coli* JM109-B23, containing the plasmid pB23, was deposited with the Fermentation Research Institute Agency of Industrial Science and Technology (FRI), 1-1-3 Yatabe-cho Higashi, Tsukuba-gun, Ibarakiken, Japan as FERM P-8971, on Sep. 19, 1986, and transferred to the international deposition under the Budapest Treaty on the International Recognition of the Deposit of Microorganisms for the Purpose of Patent Procedure as FERM BP-1459 on Sep. 1, 1987.

Determination of nucleotide sequence of A-type inclusion body gene

The nucleotide sequence of an A-type inclusion body gene of cowpox virus was determined using the plasmids pB20, pB23, and pC6. The procedure for this determination is exemplified with reference to plasmid pB20.

Five μg of DNA of the plasmid pB20 were digested with 5 units each of SphI and BamHI, and the digest was extracted with phenol/chloroform to obtain a DNA fragment. Although the BamHI end can be attacked by exonuclease III, the SphI end can not be attacked by exonuclease III. Therefore, digestion of the SphI-BamHI fragment with exonuclease III provides various DNA fragments having different lengths. The DNA was digested with 24 units of exonuclease III. During the digestion, a 1/10 volume of reaction mixtures was removed at one minute intervals, and the removed reaction mixture was extracted with phenol/-chloroform to obtain exonuclease III-digested DNA fragments. The DNA fragments were then treated with 0.1 units of S1 nuclease for 30 minutes, and the reaction mixture was extracted with phenol/chloroform to obtain DNA. To the reaction solution (60 μl) were added 1.5 μl of 0.2M magnesium chloride, 2 μl each of four kinds of 5 mM deoxyribonucleotides, and one unit of a Klenow fragment, and after 30 minutes at room temperature, ligation was carried out by adding 350 units of T4 DNA ligase. Next, 1/50 volume of the reaction mixture was used to transform *E. coli* JM109, and a plasmid DNA was extracted from the resulting colonies by the alkaline extraction method.

The extracted DNA was then subjected to sequencing by the dideoxy method of Sanger et al.

FIGS. 3A to 3J represent a nucleotide sequence of a DNA fragment containing an A-type inclusion body structural gene and a promoter region therefor. The promoter is contained in a nucleotide sequence from the positions-576 to -1, and a nucleotide sequence from positions 1 to 3852 forms an open reading frame coding for a protein comprising 1284 amino acids which are shown by lower lines in FIG. 3A to 3I. The size of this reading frame conforms to the molecular weight of the A-type inclusion body protein, i.e., 160,000 Daltons, measured by SDS-polyacrylamide gel electrophoresis. Moreover, the 5′-terminal nucleotide sequence in the open reading frame is analogous with those of other late promoters of vaccinia virus; which confirms that A-type inclusion bodies are formed during latter phase of the infection, and thus that the cloned gene of the present invention is actually a gene for the A-type inclusion body protein.

Note, the amino acid composition of the major protein of A-type inclusion body is estimated from the determined nucleotide sequence, as follows.

| Amino acid | Number of residue | Amino acid composition (%) | Amino acid | Number of residue | Amino acid composition (%) |
|---|---|---|---|---|---|
| Ala | 47 | (3.7) | Arg | 123 | (9.6) |
| Asn | 63 | (4.9) | Asp | 110 | (8.6) |
| Cys | 26 | (2.0) | Gln | 37 | (2.9) |
| Glu | 161 | (12.5) | Gly | 45 | (3.5) |
| His | 12 | (0.9) | Ile | 69 | (5.4) |
| Leu | 123 | (9.6) | Lys | 99 | (7.7) |
| Met | 21 | (1.6) | Phe | 28 | (2.2) |
| Pro | 36 | (2.8) | Ser | 100 | (7.8) |
| Thr | 70 | (5.4) | Trp | 4 | (0.3) |

-continued

| Amino acid | Number of residue | Amino acid composition (%) | Amino acid | Number of residue | Amino acid composition (%) |
| --- | --- | --- | --- | --- | --- |
| Tyr | 51 | (4.0) | Val | 59 | (4.6) |
| Acidic amino acids (Asp, Glu) | | | | 271 | (21.1) |
| Basic amino acids (Arg, His, Lys) | | | | 234 | (18.2) |

Identification of A-type inclusion body-related gene in vaccinia virus genome

Figure 1:
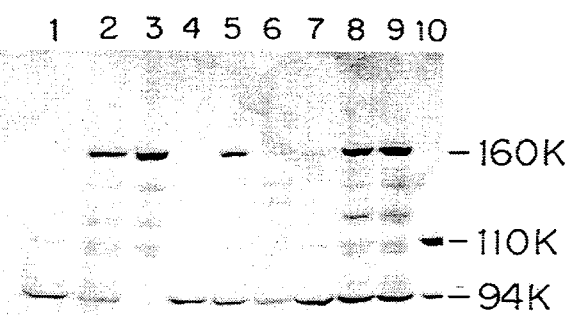
FIG. 1 is a photograph of electrophoresis showing a result of Western blotting wherein expression products of vaccinia virus-infected animal cells (CV-1 cell line) transfected with a plasmid are detected using an anti-A-type inclusion body antibody; wherein lane 1 represents products of vaccinia WR-infected cells, lane 2 represents vaccinia WR and cowpox CPRO6-coinfected cells, lane 3 represents products of cowpox-infected cells, lane 4 represents products of pUC 18-transfected cells, lane 5 represents products of p0804-transfected cells, lane 6 represents products of pB6-transfected cells, lane 7 represents products of pB20-transfected cells, lane 8 represents products of pB23-transfected cells, lane 9 represents products of pC3-transfected cells, and lane 10 represents products of pC6-transfected cells.

As shown in FIG. 1, vaccinia virus provides a protein of 94,000 Daltons which is reactive with an anti-A-type inclusion body antibody. Therefore, it can be reasonably considered that the vaccinia virus DNA contains an A-type inclusion body-related gene, and if so, such a region may be a nonessential region and have a strong promoter.

To confirm the above-estimation, the present inventors tested DNA extracted from vaccinia virion and cowpox virion by Southern blotting. More specifically, a DNA fragment of about 1 Kb at the right side of the PstI site in the A-type inclusion body gene in FIG. 2 was separated and labeled with $\alpha$-$^{32}$PdCTP using an Amersham nick-translation kit, and a labeled DNA fragment with a specific activity of about $5 \times 10^6$ cpm/$\mu$g was prepared and used as a probe.

On the other hand, DNAs were extracted from vaccinia virion and cowpox virion. The DNAs were then cleaved with HindIII or SalI, separated by 0.6% agarose gel electrophoresis, and the separated DNA fragments were electrophoretically transferred to a nylon membrane (Zetaprobe). The DNA fragments on the nylon membrane were allowed to hybridize with the above-mentioned probe under the condition of a 50% formamide, 5×SSC, 0.1% SDS, 5×Denhardt's solution, 250 $\mu$g/ml salmon sperm DNA, and 25 mM sodium phosphate (pH 6.5) and incubation overnight at 42° C.

Figure 4:
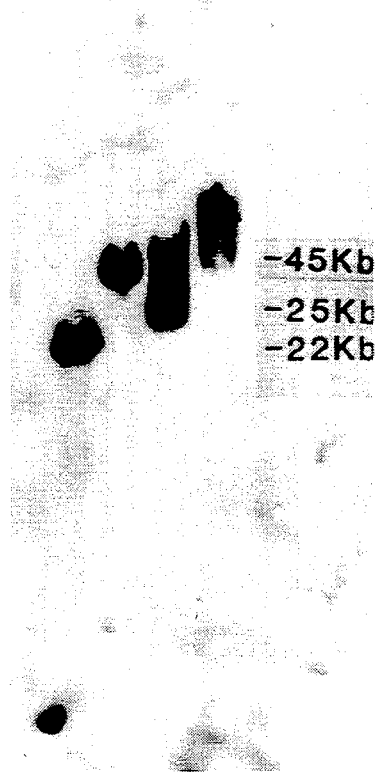
FIG. 4 represents a result of Southern blotting for cowpox virus DNA and vaccinia virus DNA using a cloned A-type inclusion body gene as a probe, wherein lane 1 represents a result of cowpox virus DNA cleaved with SalI, lane 2 represents a result of cowpox virus DNA cleaved with HindIII, lane 3 represents a result of vaccinia virus DNA cleaved with SalI, and lane 4 represents a result of vaccinia virus DNA cleaved with HindIII.

The results are shown in FIG. 4. In FIG. 4, lane 1 represents the result of a cowpox virus DNA cleaved with SalI, lane 2 represents the result of a cowpox virus DNA cleaved with HindIII, lane 3 represents the result of a vaccinia virus DNA cleaved with SalI, and lane 4 represents the result of a vaccinia virus DNA cleaved with HindIII.

As seen from FIG. 4, the cleavage of a cowpox virus DNA with SalI provided a DNA fragment of about 22 Kb reactive with the probe, which corresponds to a molecular weight of the DNA fragment 0804 in the plasmid p0804; the cleavage of the cowpox virus DNA with HindIII provided a DNA fragment of about 45 to 50 Kb reactive with the probe; the cleavage of the vaccinia virus DNA with SalI provided a DNA fragment of about 25 to 30 Kb reactive with the probe; and the cleavage of the vaccinia virus DNA with HindIII provided a 45 to 50 Kb DNA fragment reactive with the probe.

These results suggest that the vaccinia virus contains a gene corresponding to the A-type inclusion body gene of cowpox virus. Moreover, since the DNA fragments derived from vaccinia virus reacted with the probe were derived from the A-type inclusion body gene of cowpox virus in the condition of a high stringency, this suggests the possibility of a homologous recombination of the cowpox A-type inclusion body gene with the vaccinia virus A-type inclusion body-related gene, and therefore, the possibility of a transfer of an exogeneous gene incorporated in the cowpox virus A-type inclusion body gene to the vaccinia virus DNA. Accordingly, the A-type inclusion body gene of cowpox virus origin of the present invention is promising as an intermediate vector for an insertion of an exogeneous antigen gene into vaccinia virus, to construct the recombinant vaccinia virus as a live vaccine.

Figure 5:
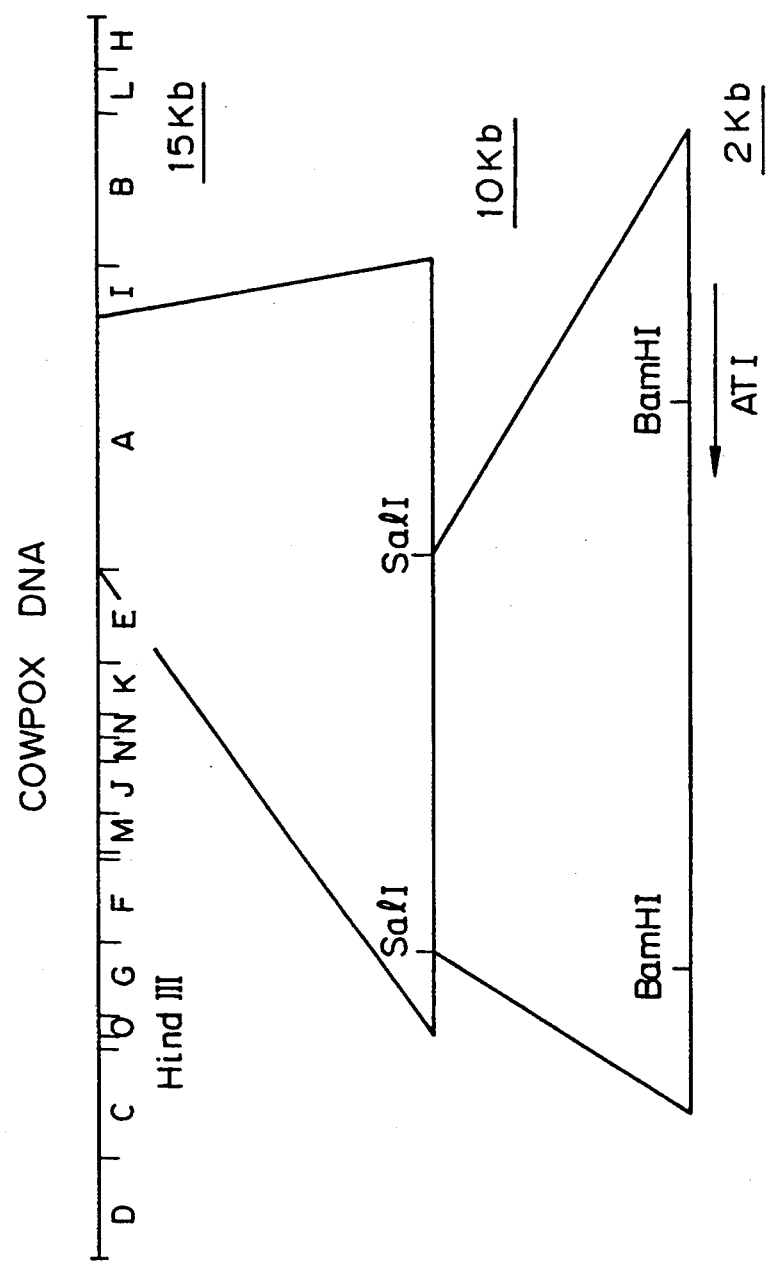
FIG. 5 represents the position of an A-type inclusion body gene in cowpox virus DNA; and, FIG. 6 represents the position of a SalI fragment containing an A-type inclusion body-related gene in vaccinia virus DNA.
Figure 6:
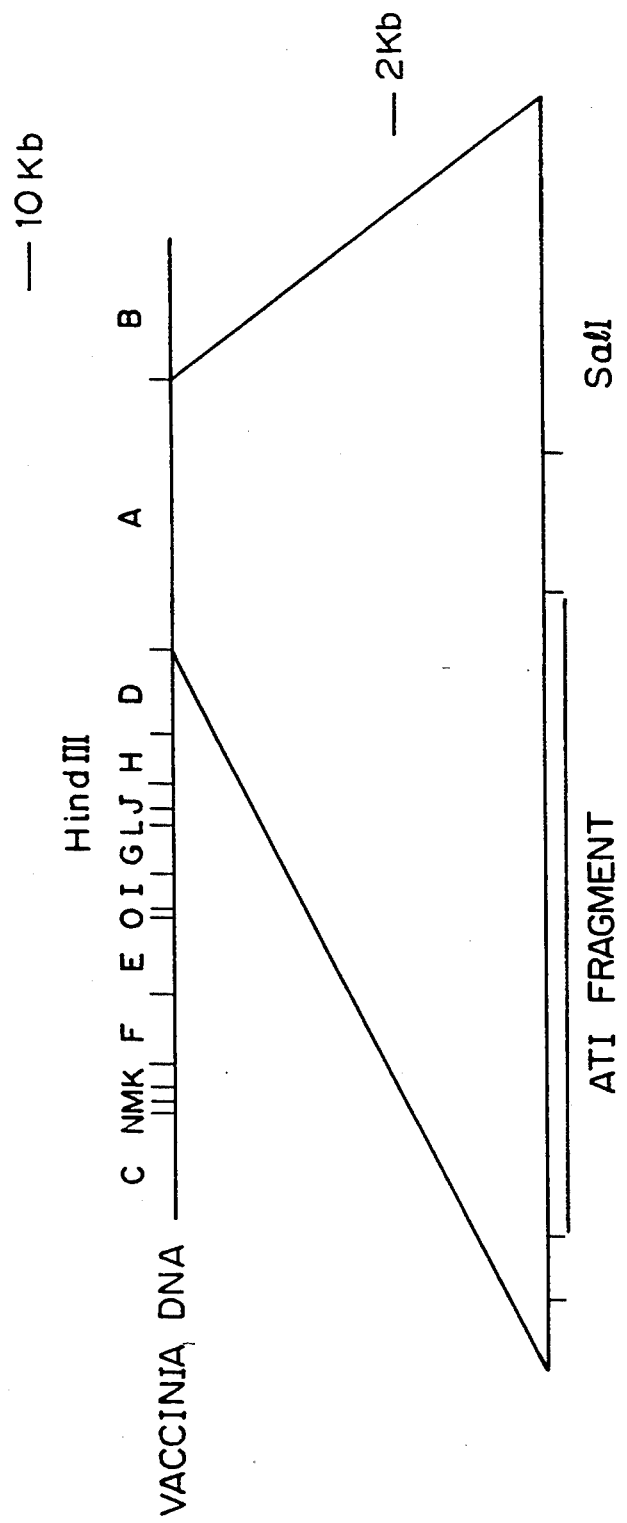

Localization of A-type inclusion body-related gene in cowpox virus genome and vaccinia virus genome Taking into consideration the above-mentioned result of Southern blotting and the report in J. Gen. Virol. 45, 51–63, 1979; and Nucl. Acids Res. 12, 4835–4848, 1984, the localization of an A-type inclusion body gene in the cowpox virus genome and its related gene in vaccinia virus genome are shown in FIGS. 5 and 6, respectively.

Preparation of anti-A-type inclusion body antiserum

An anti-A-type inclusion body antiserum used for the detection of gene expression products in the previous experiments was prepared as follows:

(1) Isolation of purified A-type inclusion bodies as an antigen

To obtain sufficient A-type inclusion bodies in a highly purified state, a new procedure was devised. Vero cells ($2 \times 10^8$), which had been infected with CPRO6 for 24 hrs at a multiplicity of 5 plaque forming unit (PFU) per cell, were scraped off the walls of Roux bottles, and pelleted by low speed centrifugation. The cells were washed twice with a 50 ml TNC buffer (10 mM Tris-HCl, pH 7.2, 0.15M NaCl, and 1 mM CaCl$_2$), and suspended in 10 ml of 10 mM Tris-HCl, pH 7.2 and 1 mM CaCl$_2$. The cells were allowed to swell for 10 min at 0° C., lysed by 10–15 strokes of a Dounce homogenizer, and tonicity then immediately restored by the addition of ¼ volume of 0.75M Tris-HCl, pH 7.2. The lysate was centrifuged at 200×g for 30 sec to sediment nuclei, the supernatant sonicated 4 times for 30 sec and centrifuged at 800×g for 10 min. It was necessary to use tubes made of polyallomer or polypropylene for centrifugation, in order to prevent loss of the A-type inclusion bodies due to adsorption to the centrifuge tube walls. The pellet containing the A-type inclusion bodies was suspended in a 25 ml TD buffer (0.15M Tris-HCl, pH 7.2 and 0.1% sodium deoxycholate) with the aid of 15 secs sonication, and was incubated for 30 min at 0° C. The material was then centrifuged at 800×g for 10 min, resuspended by brief sonication in 25 ml of 0.15M Tris-HCl, pH 7.2 and 0.1% Triton X-100, and recentrifuged. The pellet obtained was resuspended in a 2 ml TD buffer, and layered onto a discontinuous sucrose gradient composed of 10 ml of 60% (w/v), 70%, and 85% sucrose in 10 mM Tris-HCl, pH 7.2. When this was centrifuged for 60 min at 75,000×g, the A-type inclusion bodies floated at the interphase between 70% and 85% sucrose. This concentrated A-type inclusion body fraction was collected from a hole at the bottom of the tubes, and after 8-fold dilution with a TD buffer, was centrifuged at 2,000×g for 20 min. In some experiments the sucrose density gradient centrifugation was omitted.

(2) Preparation of anti-A-type inclusion body antiserum

To raise antiserum against the major A-type inclusion body polypeptide, purified A-type inclusion bodies were dissolved in a dissociation buffer and electrophoresed on preparative sodiumdodecyl sulfate-polyacrylamide gels (PAGE). The 160-kDa band was excised and pulverized by a Teflon homogenizer, and gel pieces containing approximately 500 μg of the A-type inclusion body polypeptide were injected 3 times with Freund's complete adjuvant at 2 weeks intervals into a rabbit. The rabbit was bled one week after the final injection. The obtained blood was then processed according to a conventional procedure to prepare the target antiserum.

According to the present invention, a gene coding for a major protein of A-type inclusion body in poxvirus and an expression control region, especially a promoter related to the gene, are provided. When the gene is transfected to animal cells which have been infected with vaccinia virus, expression of the A-type inclusion body gene is confirmed.

The gene region coding for a major protein of A-type inclusion body is nonessential for the proliferation of virus, and moreover, the A-type inclusion body gene of cowpox virus is extremely homologous with the A-type inclusion body-related gene of the vaccinia virus. Therefore, the A-type inclusion body gene of cowpox virus is useful as an intermediate vector for transfer of an exogeneous antigen gene into vaccinia virus, to construct a recombinant vaccinia virus as a live vaccine.

Moreover, since a promoter of the A-type inclusion body gene is strong, the promoter is useful for expression of an exogeneous antigen gene in a recombinant vaccinia virus.

We claim:

1. A plasmid for homologous recombination with vaccinia virus, comprising an exogenous antigen gene inserted into a gene coding for a 160 Kd major protein of A-type inclusion body of cowpox virus.

2. A plasmid according to claim 1, wherein the plasmid further comprises a promoter of a gene for a 160 Kd major protein of A-type inclusion body of cowpox virus.

3. An isolated or purified DNA fragment comprising a promoter of a gene for a 160 Kd major protein of A-type inclusion body of cowpox virus.

4. A DNA fragment consisting essentially of the promoter which controls transcription of the 160 kDA A-type inclusion body protein of cowpox virus.

* * * * *

UNITED STATES PATENT AND TRADEMARK OFFICE
CERTIFICATE OF CORRECTION

PATENT NO. : 5,426,051
DATED : June 20, 1995
INVENTOR(S) : SHIDA, et al

It is certified that error appears in the above-indentified patent and that said Letters Patent is hereby corrected as shown below:

TITLE PAGE, left column
        item [73] to read
-- Assignee:  Toa Nenryo Kogyo Kabushiki Kaisha,
              Tokyo, Japan, and President of
              Kyoto University, Kyoto, Japan --

Signed and Sealed this

Fifteenth Day of October, 1996

*Attest:*

BRUCE LEHMAN

*Attesting Officer*      *Commissioner of Patents and Trademarks*